(12) United States Patent
Fujii et al.

(10) Patent No.: US 11,933,752 B2
(45) Date of Patent: Mar. 19, 2024

(54) GAS SENSOR AND FUEL CELL VEHICLE

(71) Applicant: Panasonic Intellectual Property Management Co., Ltd., Osaka (JP)

(72) Inventors: Satoru Fujii, Osaka (JP); Zhiqiang Wei, Osaka (JP); Kazunari Homma, Kyoto (JP); Shinichi Yoneda, Kyoto (JP); Yasuhisa Naito, Ibaraki (JP); Hisashi Shima, Ibaraki (JP); Hiroyuki Akinaga, Ibaraki (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 703 days.

(21) Appl. No.: 16/520,219

(22) Filed: Jul. 23, 2019

(65) Prior Publication Data
US 2019/0346391 A1 Nov. 14, 2019

Related U.S. Application Data

(63) Continuation of application No. PCT/JP2018/001992, filed on Jan. 23, 2018.

(30) Foreign Application Priority Data

Jan. 31, 2017 (JP) .................................. 2017-016307

(51) Int. Cl.
*G01N 27/12* (2006.01)
*G01N 27/414* (2006.01)
(Continued)

(52) U.S. Cl.
CPC ....... *G01N 27/125* (2013.01); *G01N 27/4141* (2013.01); *G01N 33/005* (2013.01); *H01M 8/04* (2013.01)

(58) Field of Classification Search
CPC .... G01N 27/12; G01N 27/125; G01N 27/128; G01N 27/4141; G01N 33/005
See application file for complete search history.

(56) References Cited

U.S. PATENT DOCUMENTS

| | | | |
|---|---|---|---|
| 4,936,956 A | 6/1990 | Wrighton | |
| 2005/0074970 A1* | 4/2005 | Serina | G01N 33/005 438/686 |

(Continued)

FOREIGN PATENT DOCUMENTS

| | | |
|---|---|---|
| CN | 1820196 A | 8/2006 |
| EP | 2490012 A1 | 8/2012 |

(Continued)

OTHER PUBLICATIONS

Feng, Chang Dong, Yasuhiro Shimizu, and Makoto Egashira. "Effect of Gas Diffusion Process on Sensing Properties of SnO2 Thin Film Sensors in a SiO2/SnO2 Layer-Built Structure Fabricated by Sol-Gel Process." Journal of the Electrochemical Society 141.1 (1994): 220. "Feng" (Year: 1994).*

(Continued)

*Primary Examiner* — Kristina M Deherrera
*Assistant Examiner* — Fatemeh Esfandiari Nia
(74) *Attorney, Agent, or Firm* — Rimon, P.C.

(57) ABSTRACT

A gas sensor includes: a gas-sensitive body layer disposed above a substrate and including a metal oxide layer; a first electrode on the gas-sensitive body layer; and a second electrode on the gas-sensitive body layer, being apart from the first electrode by a gap. The gas-sensitive body layer has a resistance change characteristic that reversibly transitions to a high-resistance state and a low-resistance state on basis of a voltage applied across the first electrode and the second electrode. At least a part of the gas-sensitive body layer is exposed to the gap. The gas-sensitive body layer has a resistance that decreases when gas containing a hydrogen atom is in contact with the second electrode.

14 Claims, 9 Drawing Sheets

(51) Int. Cl.
G01N 33/00 (2006.01)
H01M 8/04 (2016.01)

(56) References Cited

U.S. PATENT DOCUMENTS

| | | | |
|---|---|---|---|
| 2006/0169024 | A1 | 8/2006 | Shoji |
| 2008/0232153 | A1* | 9/2008 | Naitoh .................. G11C 11/56 |
| | | | 257/E29.325 |
| 2009/0251199 | A1 | 10/2009 | Naitoh et al. |
| 2012/0206156 | A1* | 8/2012 | Karakaya ........... G01N 27/4148 |
| | | | 324/705 |
| 2013/0130261 | A1* | 5/2013 | Prodromakis .......... G01N 27/60 |
| | | | 422/82.01 |
| 2013/0186178 | A1 | 7/2013 | Usagawa |
| 2013/0250658 | A1 | 9/2013 | Wei et al. |
| 2016/0018356 | A1* | 1/2016 | Shankar ............... G01N 27/128 |
| | | | 438/49 |
| 2017/0131227 | A1 | 5/2017 | Homma et al. |
| 2017/0141302 | A1* | 5/2017 | Bessonov ............ H01L 45/146 |

FOREIGN PATENT DOCUMENTS

| | | |
|---|---|---|
| EP | 2891883 A1 | 7/2015 |
| JP | 59-058348 A | 4/1984 |
| JP | 59-058348 B2 | 4/1984 |
| JP | H0961390 A * | 3/1997 |
| JP | 2005030907 A * | 2/2005 |
| JP | 2006128438 A * | 5/2006 |
| JP | 2009-042213 A | 2/2009 |
| JP | 2010-197074 A | 9/2010 |
| JP | 4919146 B2 | 4/2012 |
| JP | 2013068567 A | 4/2013 |
| JP | 2013068567 A * | 4/2013 |
| JP | 5352032 B2 | 11/2013 |
| JP | 2015114274 A | 6/2015 |
| JP | 2015200626 A * | 11/2015 |
| JP | 5858706 B2 * | 2/2016 |
| JP | 2018072146 A * | 5/2018 ......... G01N 27/4141 |
| KR | 20120121511 A * | 11/2012 |
| WO | 2012/043071 A1 | 4/2012 |
| WO | 2013/051267 A1 | 4/2013 |
| WO | 2017/037984 A1 | 3/2017 |

OTHER PUBLICATIONS

JP-5858706-B2-English (Year: 2016).*
JP-2006128438-A-English (Year: 2006).*
KR-20120121511-A-English (Year: 2012).*
JP-2005030907-A-English (Year: 2005).*

International Search Report issued in corresponding International Patent Application No. PCT/JP2018/001992, dated Apr. 24, 2018, with English translation.
J. Yu, et al., "Hydrogen gas sensing properties of Pt/Ta2O5 Schottky diodes based on Si and SiC substrates", Sensors and Actuators A: Physical, vol. 172, 2011, pp. 9-14.
Toshiyuki USAGAWA, et al., "A Novel Pt-Ti-O Gate Si-Metal-Insulator-Semiconductor Field-Effect Transistor Hydrogen Gas Sensor", IEEE Sensors 2010 Conference, pp. 2145-2148.
Ikuo Takahashi, "Catalytic Combustion Type Hydrogen Gas Sensor", Journal of the Surface Finishing Society of Japan, vol. 57, No. 4, 2006, pp. 25-28, with partial English translation.
Hisao Kitaguchi, "The present situation and some subjects of the hydrogen gas sensor", Journal of the Hydrogen Energy Systems Society of Japan, vol. 30, No. 2, 2005, pp. 35-40, with partial English translation.
B. Majkusiak, et al., "Theoretical Limit for the SiO2 Thickness in Silicon Mos Devices", D. Flandre et al. (eds.), Science and Technology of Semiconductor-On-Insulator Structures and Devices Operating in a Harsh Environment, Kluwer Academic Publishers, 2005, pp. 309-320.
R. Zhang, et al., "Enabling selectivity and fast recovery of ZnO nanowire gas sensors through resistive switching," Sensors and Actuators B: Chemical, vol. 238, Jul. 16, 2016, pp. 357-363, XP055649672.
S. Herbertz et al., "On-chip planar hydrogen sensor with submicrometer spatial resolution," Sensors and Actuators B: Chemical, vol. 221, Jun. 29, 2015, pp. 401-405, XP029282857.
A. Mozalev et al., "Formation and gas-sensing properties of a porous-alumina-assisted 3-D niobium-oxide nanofilm," Sensors and Actuators B: Chemical, vol. 229, Feb. 8, 2016, pp. 587-598, XP029464566.
Extended European Search Report issued in corresponding European Patent Application No. 18748776.4, dated Dec. 18, 2019.
Tournier, G. et al., "Selective filter for SnO2-based gas sensor: application to hydrogen trace detection," Sensors and Actuators B: Chemical, May 13, 2005, vol. 106, Issue 2, pp. 553-562.
Office Action issued in corresponding Japanese Patent Application No. 2017-016307, dated Jul. 7, 2020.
Chinese Office Action issued in corresponding Chinese Aatent Application No. 201880008855.5, dated May 18, 2021, with English Search Report.
Office Action issued for the corresponding European Patent Application No. 18748776.4, dated Oct. 22, 2021.
H. Kwon et al., "Highly-sensitive H2 sensor operating at room temperature using Pt/TiO2 nanoscale Schottky contacts," Sensor and Actuators B: Chemical, 2017, pp. 985-992.
Rule 115(1) EPC Summons to attend oral proceedings in EP Application No. 18 748 776.4 dated Oct. 10, 2023.
Plecenik, T., Sensors and Actuators B 207 (2015) 351-361, "Fast highly-sensitive room-temperature semiconductor gas sensor based on the nanoscale Pt-TiO2-Pt sandwich" published Oct. 14, 2014.

* cited by examiner

GAS SENSOR AND FUEL CELL VEHICLE

CROSS REFERENCE TO RELATED APPLICATIONS

This application is a U.S. continuation application of PCT International Patent Application Number PCT/JP2018/001992 filed on Jan. 23, 2018, claiming the benefit of priority of Japanese Patent Application Number 2017-016307 filed on Jan. 31, 2017, the entire contents of which are hereby incorporated by reference.

BACKGROUND

1. Technical Field

This disclosure relates to a gas sensor including a gas-sensitive body layer, and the like.

2. Description of the Related Art

Hydrogen energy has been recently gathering attention as a solution to environmental problems. As specific measures therefore, fuel cell vehicles using hydrogen as fuel have been starting to be sold. Accordingly, the development of infrastructures including hydrogen stations is also gathering attention. In order to realize a hydrogen energy-based society, it is urgently necessary to develop laws, for example, reconsider safety standards. Further, the importance of hydrogen gas sensing devices is also increasing in the safety aspect in terms of tangible factors.

As the types of the hydrogen gas sensing devices, types such as a contact combustion type, a semiconductor type, and a gas heat conduction type are used. The contact combustion type is a type using catalytic combustion heat obtained by a catalyst (Pt, Pd, and the like) of combustible gas. The semiconductor type is a type using the change in electrical conductivity caused by gas adsorption on a metal oxide semiconductor surface. The gas heat conduction type is a type using the difference in heat conduction between target gas and standard gas.

In addition, in a gas sensing device of the related art, a heating heater is installed adjacent to a gas detecting element in order to increase the detection sensitivity of the gas detecting element (for example: Japanese Unexamined Patent Application Publication No. S59-58348; Japanese Patent No. 5352032; Sensors and Actuators A 172(2011) 9-14; IEEE SENSORS 2010 Conference, 2145-2148; Journal of The Surface Finishing Society of Japan Vol. 57, No. 4, 2006, pp 267-270; Journal of The Hydrogen Energy Systems Society of Japan Vol. 30, No. 2 (2005), pp 35-40; B. Majkusiak and et al "THEORETICAL LIMIT FOR THE SiO2 THICKNESS IN SILICON MOS DEVICES" D. Flandre et al. (eds.), Science and Technology of Semiconductor-On-Insulator Structures and Devices Operating in a Harsh Environment, 309-320.c 2005 Kluwer Academic Publishers. Printed in the Netherlands). In the gas sensing device, the ambient temperature of the gas detecting element is normally maintained to be 100° C. or more at the time of measurement by the heating heater.

SUMMARY

However, as in the gas sensing device of the related art, when the gas detecting element is heated to 100° C. or more, an electricity consumption of about 100 mW is necessary at minimum. Therefore, when the gas sensing device is used in a constant ON state, the electricity consumption becomes extremely high. In addition, in order to sense the hydrogen gas, hydrogen atoms generated when the hydrogen gas is decomposed at an electrode surface need to be diffused in the electrode and reach a gas-sensitive body. At this time, the gas sensing speed becomes faster when the speed at which the hydrogen atoms reach the gas-sensitive body layer is fast. Therefore, the improvement of the gas sensing speed in a low temperature operation is a challenge.

This disclosure has been made to solve the abovementioned problem, and an object thereof is to provide a gas sensor capable of sensing gas containing hydrogen atoms with low electricity consumption and at high speed, and the like.

In accordance with an aspect of the present disclosure, there is provided a gas sensor, including: a gas-sensitive body layer disposed above a substrate and including a metal oxide layer; a first electrode disposed at a same layer level as a layer level of the gas-sensitive body layer above the substrate or disposed on the gas-sensitive body layer; and a second electrode disposed at a same layer level as a layer level of the gas-sensitive body layer above the substrate or disposed on the gas-sensitive body layer, the second electrode being apart from the first electrode by a gap, wherein: the gas-sensitive body layer has a resistance change characteristic that reversibly transitions to a high-resistance state and a low-resistance state on basis of a voltage applied across the first electrode and the second electrode; at least a part of the gas-sensitive body layer is exposed to an area corresponding to the gap; and the gas-sensitive body layer has a resistance that decreases when gas containing a hydrogen atom is in contact with the second electrode.

In accordance with another aspect of the present disclosure, there is provided a fuel cell vehicle, including: a passenger compartment; a gas tank compartment in which a tank of hydrogen gas is arranged; a fuel cell compartment in which a fuel cell is arranged; and the above-described gas sensor, wherein the gas sensor is arranged in at least one of the gas tank compartment and the fuel cell compartment.

According to this disclosure, the gas sensor capable of sensing the gas containing hydrogen atoms with low electricity consumption and at high speed, and the like can be provided.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

Figure 1:
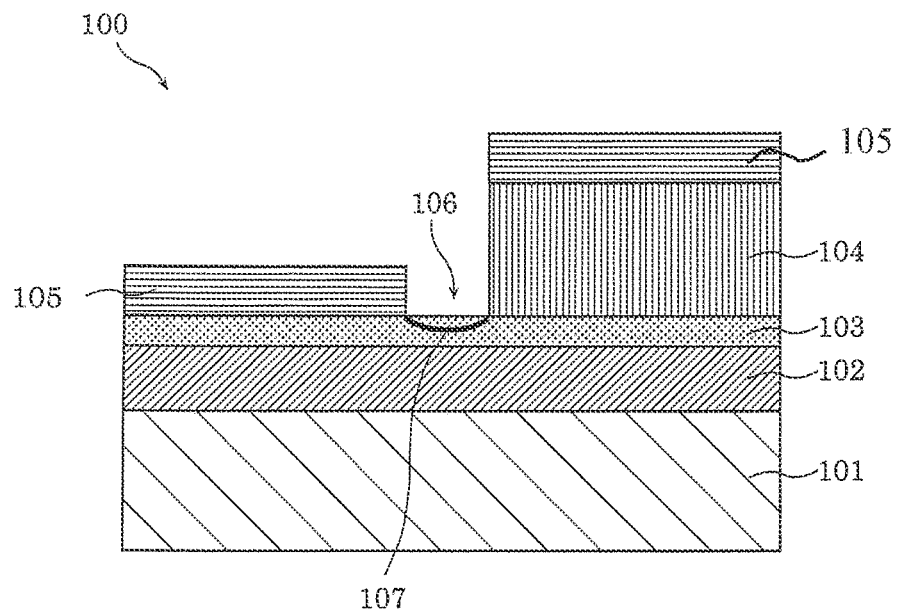
FIG. 1 is a cross-sectional view illustrating an example of the configuration of a gas sensor according to Embodiment 1.

DETAILED DESCRIPTION OF THE EMBODIMENTS (Underlying Knowledge of this Disclosure)

First, the underlying knowledge of this disclosure is described.

As the result of intensive studies, the inventors of the present disclosure have found that the gas sensor of the related art has the following problems.

As the hydrogen gas sensing device, the contact combustion type, the semiconductor type, and the gas heat conduction type have been hitherto mainly used in Japan. The contact combustion type is a sensing device using catalytic combustion heat obtained by a catalyst (Pt, Pd, and the like) of combustible gas. In the contact combustion-type hydrogen gas sensing device, as the concentration of the hydrogen gas rises, the element temperature rises due to combustion, and the resistance increases. The sensor output is linear with respect to the gas concentration, but there is a problem in gas selectivity.

The semiconductor-type hydrogen gas sensing device uses the change in electrical conductivity caused by gas adsorption on a metal oxide semiconductor surface. In the semiconductor-type hydrogen gas sensing device, the sensor output is logarithmic with respect to the gas concentration, and hence the sensitivity is high even in low-concentration regions.

The gas heat conduction-type hydrogen gas sensing device uses the difference in heat conduction between target gas and standard gas. In the gas heat conduction-type hydrogen gas sensing device, the heat conductivity of the hydrogen gas is higher than other combustible gas. Therefore, the gas heat conduction-type hydrogen gas sensing device is suitable for sensing especially in high-concentration regions.

A hydrogen gas sensing device having a MIM structure obtained by laminating an insulating film and a metal film described in PTL 1 is classified as the semiconductor type. In the hydrogen gas sensing device having a MIM structure, an insulating film obtained by adding a predetermined amount of palladium and glass to tantalum pentoxide ($Ta_2O_5$) is used as the gas-sensitive insulating film, and Pt is used as the upper and lower sandwiching metal electrodes. However, there is no description on the detailed mechanism. Thus, description can be made as follows when a phenomenon similar to that of the mechanism described in NPL 1 relating to a gas sensing device (Pt—$Ta_2O_5$—Si) using a MIS structure is assumed to be caused.

When gas containing hydrogen gas comes into contact with a surface of Pt that is a catalytic metal, for example, the hydrogen gas is decomposed into hydrogen atoms by the catalysis of Pt. Further, the decomposed hydrogen atoms are diffused in a Pt electrode and reach tantalum pentoxide ($Ta_2O_5$) that is the gas-sensitive body. The hydrogen atoms that have reached tantalum pentoxide ($Ta_2O_5$) reduce tantalum pentoxide ($Ta_2O_5$) and are oxidized in accordance with the chemical reaction formula below, thereby becoming water.

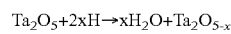

$$Ta_2O_5 + 2xH \rightarrow xH_2O + Ta_2O_{5-x}$$

At this time, it is conceived that the flow of the current is facilitated because of an oxygen defect in tantalum pentoxide formed by the hydrogen atom taking an oxygen atom from tantalum pentoxide ($Ta_2O_5$) in the gas-sensitive insulating film.

Meanwhile, when the gas containing hydrogen gas is removed from the Pt surface, it is conceived that a reversed process in accordance with the following chemical reaction formula:

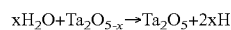

$$xH_2O + Ta_2O_{5-x} \rightarrow Ta_2O_5 + 2xH$$

occurs, the oxygen defect in tantalum pentoxide is removed, and it becomes difficult for the current to flow. By the mechanism as above, it is conceived that the MIM structure in which an insulating film obtained by adding a predetermined amount of palladium and glass to tantalum pentoxide ($Ta_2O_5$) is used as the gas-sensitive insulating film and Pt is used as the upper and lower metal electrodes sandwiching the gas-sensitive insulating film functions as a gas sensing device that senses the gas containing hydrogen atoms.

Now, when the hydrogen atoms are dissociated by Pt that is a catalytic metal, the rate of the hydrogen atoms to be dissociated from molecules containing the hydrogen atoms by the catalysis is proportional to the temperature rise. In other words, it is conceived that the detection sensitivity of the gas increases as the gas detecting element temperature rises. In the gas sensing device of the related art, in order to improve the detection sensitivity of the gas containing hydrogen atoms, the gas detecting element at the time of measurement is heated to 100° C. or more.

For example, in the gas sensing device having a MIM structure described in PTL 1, the gas detecting element temperature is raised to 400° C. by applying a predetermined voltage to a heating heater provided adjacent to the gas detecting element.

Not only in the gas sensing device having a MIM structure but also in the gas sensing device having a MIS structure using the catalysis of metal, a heating heater is installed adjacent to the gas detecting element and is normally used by maintaining the ambient temperature at 100° C. or more. For example, in the gas sensing device described in NPL 1, a temperature of 100° C. or more is needed when the MIS structure is used as a diode. In addition, a gas sensing device described in NPL 2 using a MIS structure as a transistor is operated while setting the ambient temperature of the gas detecting element to 115° C.

In addition, in a contact combustion-type gas sensing device described in NPL 3 using the catalysis of metal, the gas detecting element is heated to from 200° C. to 300° C. at the time of operation.

Further, in a hot-wire semiconductor-type gas sensing device and a gas heat conduction-type gas sensing device described in NPL 4 that do not use the catalysis of metal, the gas detecting element is heated to 100° C. or more for both types.

However, when the gas detecting element is heated to 100° C. or more, an electricity consumption of about 100 mW is necessary at minimum. Therefore, when the gas sensing device is used in a constant ON state, the electricity consumption becomes extremely high. In addition, in order to sense the hydrogen gas, hydrogen atoms generated by decomposing the hydrogen gas at an electrode surface need to be diffused in the electrode and reach the gas-sensitive body. At this time, the gas sensing speed of the gas sensing device improves as the speed at which the hydrogen atoms reach the gas-sensitive body becomes faster. Therefore, the improvement of the gas sensing speed in a low temperature operation is a challenge for the gas sensing device.

Thus, in this disclosure, a gas sensor capable of sensing gas containing hydrogen atoms with low electricity consumption and at high speed is realized by a gas sensor having the following configuration.

That is, the gas sensor according to this embodiment is a gas sensor as follows. In the gas sensor, a first electrode and a second electrode are arranged on a substrate in an opposed manner so as to form a gap, and at least a part of a gas-sensitive body layer formed by metal oxide is exposed via the gap. Further, the gas-sensitive body layer is in contact with the second electrode and includes a local region having a degree of oxygen deficiency larger than that of the metal oxide layer in the gas-sensitive body layer. Further, the resistance of the metal oxide decreases when gas molecules containing hydrogen atoms are detected. The second electrode causes catalysis that dissociates the hydrogen atoms from the gas molecules containing the hydrogen atoms. The resistance of the metal oxide layer decreases as the hydrogen atoms are dissociated from the gas molecules in a part of the second electrode in contact with the local region and the dissociated hydrogen atoms are bound to oxygen atoms in the local region of the metal oxide layer.

In a configuration in which at least one of the first electrode and the second electrode is in contact with the local region having a degree of oxygen deficiency larger than that of the metal oxide layer, the current flowing between the first electrode and the second electrode is concentrated on the local region having a larger degree of oxygen deficiency. As a result, the temperature of the local region can be raised with less current. When the temperature of the local region rises, the temperature of the surface of the second electrode also rises. In the second electrode that causes catalysis, the rate of the dissociation of the hydrogen atoms from the gas molecules containing the hydrogen atoms increases in accordance with the temperature rise.

Hereinafter, certain exemplary embodiments of the present disclosure are described in greater detail with reference to the accompanying Drawings.

In the drawings, elements regarding substantially identical structures, processing, and effects are assigned with a same reference sign, and explanation of such substantially identical elements is not repeated. Numerical values, materials, film forming methods, and the like described in the following embodiments are merely examples for explaining the embodiments according to the present disclosure in more detail, and are not intended to limit the present disclosure. Connection relationships between constituent elements described in the following embodiments are merely examples for explaining the embodiments according to the present disclosure in more detail, and connection relationships for achieving the functions of the present disclosure are not limited to the described relationships. Furthermore, the present disclosure is defined by the claims. Therefore, among the constituent elements in the following embodiments, constituent elements that are not described in independent claims that show the most generic concept of the present disclosure are described as elements constituting more desirable configurations, although such constituent elements are not necessarily required to achieve the object of the present disclosure.

Embodiment 1

[Configuration of Gas Sensor]

FIG. 1 is a cross-sectional view illustrating an example of the configuration of gas sensor 100 according to Embodiment 1.

Gas sensor 100 according to this embodiment includes substrate 101, interlayer insulating film 102 formed on substrate 101, gas-sensitive insulating film 103 that is a metal oxide layer formed on interlayer insulating film 102, first electrode 104, second electrode 105, and gap 106 formed by arranging first electrode 104 and second electrode 105 to be opposed to each other. First electrode 104 is formed on gas-sensitive insulating film 103, and second electrode 105 is formed on gas-sensitive insulating film 103 so as to have gap 106 between first electrode 104 and second electrode 105. In addition, in gap 106 formed by arranging first electrode 104 and second electrode 105 to be opposed to each other, a part of gas-sensitive insulating film 103 is exposed.

Note that, as described below, first electrode 104 and second electrode 105 are not limited to be formed on gas-sensitive insulating film 103, and may be formed above substrate 101 at the same layer level as gas-sensitive insulating film 103.

Gas-sensitive insulating film 103 is a layer in which the resistance reversibly changes on the basis of an electrical signal provided between first electrode 104 and second electrode 105. For example, gas-sensitive insulating film 103 is a layer that reversibly transitions to a high-resistance state and a low-resistance state in accordance with a voltage difference provided between first electrode 104 and second electrode 105.

Now, gas-sensitive insulating film 103 is arranged in contact with second electrode 105, and has local region 107 that is not in contact with first electrode 104 in the region of gap 106 formed by arranging first electrode 104 and second electrode 105 to be opposed to each other. In local region 107, the degree of oxygen deficiency reversibly changes in accordance with the application of an electrical pulse provided between first electrode 104 and second electrode 105. It is conceived that local region 107 includes filaments (conductive paths) formed by oxygen defection sites.

It is conceived that, in the resistance change phenomenon in gas-sensitive insulating film 103, the resistance changes as the degree of oxygen deficiency in the filaments in very small local region 107 changes when an oxidation-reduction reaction occurs in local region 107.

Note that, in this disclosure, the "degree of oxygen deficiency" is a rate of deficient oxygen with respect to the amount of oxygen forming the oxide having a stoichiometric composition (when there are a plurality of stoichiometric compositions, the stoichiometric composition of which resistance is the highest out of those stoichiometric compositions) in metal oxide. The metal oxide having a stoichiometric composition is more stable and has a higher resistance than metal oxide having other compositions.

For example, when the metal is tantalum (Ta), the oxide having the stoichiometric composition according to the abovementioned definition is $Ta_2O_5$, and hence can be expressed as $TaO_{2.5}$. The degree of oxygen deficiency of $TaO_{2.5}$ is 0%, and the degree of oxygen deficiency of $TaO_{1.5}$ is the degree of oxygen deficiency=(2.5−1.5)/2.5=40%. In addition, metal oxide with excess oxygen has a degree of oxygen deficiency that is a negative value. Note that, in this disclosure, unless otherwise noted, the degree of oxygen deficiency is described so as to include positive values, 0, and negative values.

The oxide having a small degree of oxygen deficiency has a high resistance because the oxide is closer to the oxide having a stoichiometric composition, and the oxide having a large degree of oxygen deficiency has a low resistance because the oxide is closer to the metal forming the oxide.

The "oxygen content" is a ratio of the oxygen atoms to the total number of atoms. For example, the oxygen content of $Ta_2O_5$ is a ratio (O/(Ta+O)) of the oxygen atoms to the total number of atoms, and is 71.4 atm %. Therefore, the oxygen content of the oxygen deficient-type tantalum oxide is larger than 0 and is smaller than 71.4 atm %.

Gas-sensitive insulating film 103 has local region 107. The degree of oxygen deficiency of local region 107 is larger than the degree of oxygen deficiency of gas-sensitive insulating film 103.

Local region 107 is formed in gas-sensitive insulating film 103 by applying an initial breakdown voltage across first electrode 104 and second electrode 105. Now, the initial breakdown voltage is a voltage of which absolute value is larger than that of an application voltage applied across first electrode 104 and second electrode 105 in order to cause the state to reversibly transition to a high-resistance state and a low-resistance state. Note that, as the initial breakdown voltage, a voltage lower than the application voltage for causing the state to reversibly transition to the high-resistance state and the low-resistance state described above may be repeatedly applied or applied for a predetermined amount of time. By the initial breakdown, local region 107 in contact with second electrode 105 and first electrode 104 is formed.

In this disclosure, a local region means a region out of gas-sensitive insulating film 103 through which the current dominantly flows when voltage is applied across first electrode 104 and second electrode 105. Note that local region 107 means a region including a set of a plurality of filaments (conductive paths) formed in gas-sensitive insulating film 103. That is, the resistance change in gas-sensitive insulating film 103 is realized through local region 107. Therefore, when a drive voltage is applied to gas-sensitive insulating film 103, the current dominantly flows through local region 107 including the filaments.

In addition, local region 107 is a resistance change layer that reversibly transitions to a high-resistance state and a low-resistance state on the basis of the voltage difference provided between first electrode 104 and second electrode 105. Local region 107 may be in either of the high-resistance state and the low-resistance state. In both states, the state changes to a state with a lower resistance when the gas molecules containing the hydrogen atoms reach a place near second electrode 105 that causes catalysis. Therefore, the gas molecules containing the hydrogen atoms can be sensed.

However, the rate of the resistance change that occurs when the gas molecules containing the hydrogen atoms reach the place near second electrode 105 that causes catalysis becomes larger when local region 107 is maintained in a high-resistance state as compared to when local region 107 is maintained in a low-resistance state. Therefore, it is preferred that the local region be maintained in a high-resistance state.

The size of local region 107 may be small, and is a size by which one end thereof does not come into contact with first electrode 104. Local region 107 has a size by which the filaments necessary for at least causing the current to flow can be secured. The output value of the current flowing through gas-sensitive insulating film 103 differs depending on the size and the resistance state of local region 107.

The formation of the filaments in local region 107 can be described with use of a percolation model described in PTL 2. Now, it is assumed that the filaments are formed when the oxygen defection sites in local region 107 are connected. The percolation model is a model based on a theory that the probability of the connection of the oxygen defection sites (hereinafter simply referred to as a defection site) and the like being formed increases when the density of the defection sites and the like exceeds a certain threshold value given a random distribution of the defection sites and the like in local region 107. Note that the metal oxide is herein formed by a metal ion and an oxygen ion. Further, the "defection" means that oxygen is lacking from the stoichiometric composition in the metal oxide. Further, "the density of the defection sites" also corresponds to the degree of oxygen deficiency. In other words, when the degree of oxygen deficiency increases, the density of the defection sites increases as well.

Local region 107 may be formed in only one place or in a plurality of places in gas-sensitive insulating film 103 of gas sensor 100. The number of local regions 107 formed in gas-sensitive insulating film 103 can be checked by an electron beam absorbed current (EBAC) analysis, for example.

In order to place gas sensor 100 in a state in which the gas containing hydrogen atoms can be sensed, the resistance of gas-sensitive insulating film 103 of gas sensor 100 is set to a predetermined resistance by applying a voltage satisfying a predetermined condition across first electrode 104 and second electrode 105 by an external power supply. The resistance of gas-sensitive insulating film 103 of gas sensor 100 reversibly increases or decreases in accordance with the voltage difference in the voltage applied across first electrode 104 and second electrode 105. For example, when a pulse voltage of a predetermined polarity of which amplitude is larger than that of a predetermined threshold value voltage is applied, the resistance of gas-sensitive insulating film 103 increases or decreases. The voltage as above may be hereinafter referred to as a "voltage for writing". Meanwhile, when a pulse voltage of which amplitude is smaller than that of the threshold value voltage is applied, the resistance of gas-sensitive insulating film 103 does not change. The voltage as above may be hereinafter referred to as a "voltage for reading".

Gas-sensitive insulating film 103 is formed by an oxygen deficient metal oxide. More specifically, the metal oxide is a transition metal oxide. At least one of transition metal such as tantalum (Ta), hafnium (Hf), titanium (Ti), zirconium (Zr), niobium (Nb), tungsten (W), nickel (Ni), and iron (Fe) and aluminum (Al) may be selected as the mother metal of the transition metal oxide. The transition metal can be placed in a plurality of oxidation states, and hence different resistance states can be realized by the oxidation-reduction reaction. Now, the oxygen deficient metal oxide refers to metal oxide of which oxygen content amount (atom ratio: the rate of the number of oxygen atoms with respect to the total number of atoms) is smaller than that of the composition of metal oxide (typically, an insulator) having a stoichiometric composition, and many thereof normally behave in a semiconducting manner. By using the oxygen deficient metal oxide for gas-sensitive insulating film 103, a stable resistance change operation with excellent reproducibility can be realized in gas sensor 100.

For example, when hafnium oxide is used as the metal oxide forming gas-sensitive insulating film 103, the resistance of gas-sensitive insulating film 103 can be changed in a stable manner when x is 1.6 or more when the composition is $HfO_x$. In this case, the film thickness of the metal oxide may be from 3 nm to 4 nm.

In addition, when zirconium oxide is used as the metal oxide forming gas-sensitive insulating film 103, the resistance of gas-sensitive insulating film 103 can be changed in a stable manner when x is 1.4 or more when the composition is $ZrO_x$. In this case, the film thickness of the metal oxide may be from 1 nm to 5 nm. In addition, when tantalum oxide is used as the metal oxide forming gas-sensitive insulating film 103, the resistance of gas-sensitive insulating film 103 can be changed in a stable manner when x is 2.1 or more when the composition is $TaO_x$. The composition of the metal oxide layer can be measured with use of a Rutherford backscattering method.

The material of first electrode 104 and second electrode 105 is selected from, for example, platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), titanium nitride aluminum (TiAlN), and the like.

Specifically, second electrode 105 is formed by a material that causes catalysis that dissociates the hydrogen atoms from the gas molecules containing the hydrogen atoms such as at least one of platinum (Pt), iridium (Ir), and palladium (Pd), for example. In addition, first electrode 104 may be formed by a material of which standard electrode potential is lower than that of the metal forming first metal oxide such as tungsten (W), nickel (Ni), tantalum (Ta), titanium (Ti), aluminum (Al), tantalum nitride (TaN), and titanium nitride (TiN), for example. The standard electrode potential shows a characteristic in which oxidize becomes more difficult as the value thereof becomes higher.

In addition, a silicon single crystal substrate or a semiconductor substrate, for example, can be used as substrate 101, but substrate 101 is not limited thereto. Gas-sensitive insulating film 103 can be formed in a relatively low substrate temperature, and hence gas-sensitive insulating film 103 can be formed on a resin material and the like, for example.

In addition, gas sensor 100 may further include load elements electrically connected to gas-sensitive insulating film 103, for example, a fixed resistor, a transistor, or a diode.

[Manufacturing Method and Operation of Gas Sensor]

Next, an example of a manufacturing method of gas sensor 100 according to this embodiment is described with reference to FIG. 2A to FIG. 2C.

Figure 2A:
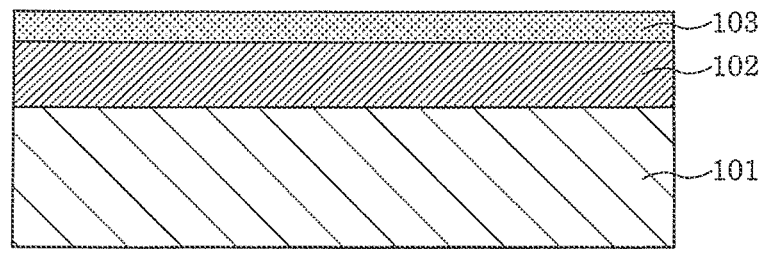
FIG. 2A is a cross-sectional view illustrating an example of a manufacturing method of the gas sensor according to Embodiment 1.

First, as illustrated in FIG. 2A, interlayer insulating film 102 having a thickness of 300 nm is formed on substrate 101 that is single crystal silicon, for example, by thermal oxidation. Then, an oxygen deficient oxide layer is formed on interlayer insulating film 102 by reactive sputtering using a Ta target, for example. As a result, gas-sensitive insulating film 103 is formed.

Figure 2B:
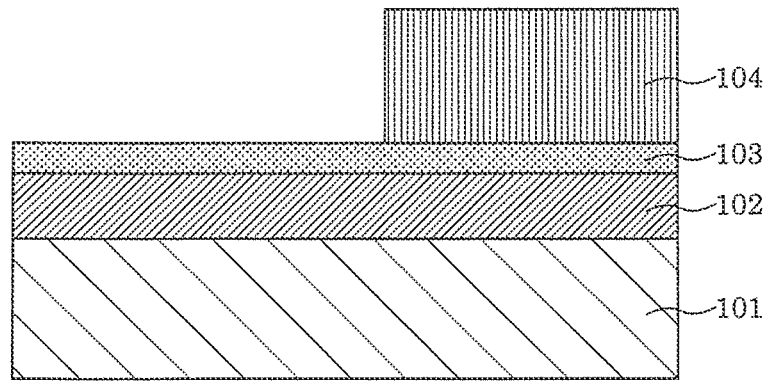
FIG. 2B is a cross-sectional view illustrating an example of the manufacturing method of the gas sensor according to Embodiment 1.

Next, as illustrated in FIG. 2B, a Ti thin film having a thickness of 25 nm, for example, is formed on gas-sensitive insulating film 103 as first electrode 104 by electron beam vapor deposition. Then, although not shown, processing is performed on first electrode 104 so as to obtain a predetermined shape by a photolithography process. Note that, the photolithography process can be omitted by using a metal mask when first electrode 104 is formed.

Figure 2C:
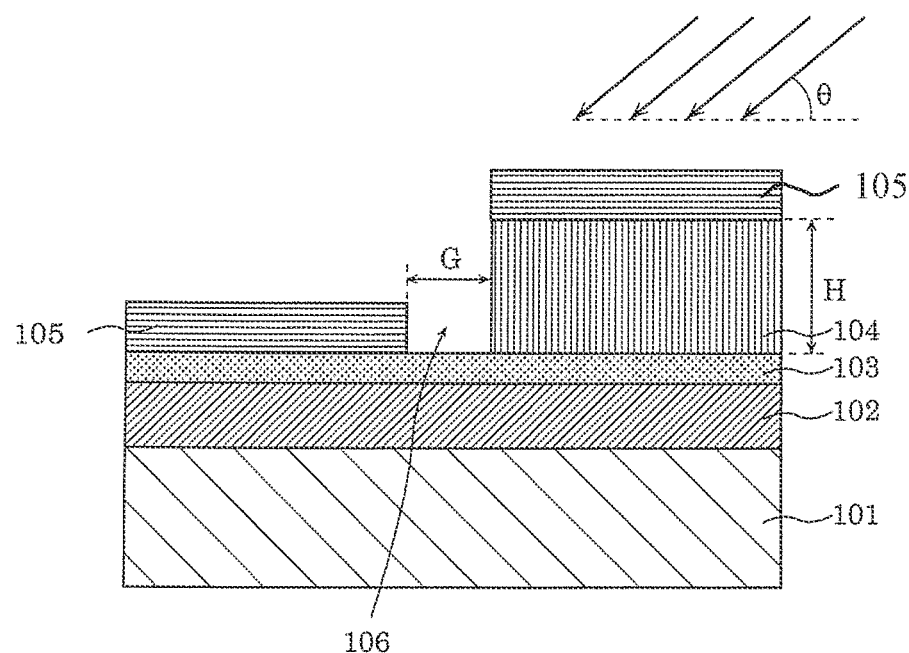
FIG. 2C is a cross-sectional view illustrating an example of the manufacturing method of the gas sensor according to Embodiment 1.

Then, as illustrated in FIG. 2C, second electrode 105 is formed by an oblique vapor deposition process. In the oblique vapor deposition process, when a material that forms second electrode 105 is vapor-deposited from the direction of angle θ with respect to substrate 101 as illustrated in FIG. 2C, the pattern of first electrode 104 having height H forms a shadow, and gap 106 having width G is formed. A Pt thin film having a thickness of 13 nm, for example, is formed on gas-sensitive insulating film 103 and first electrode 104 as second electrode 105.

Figure 2D:
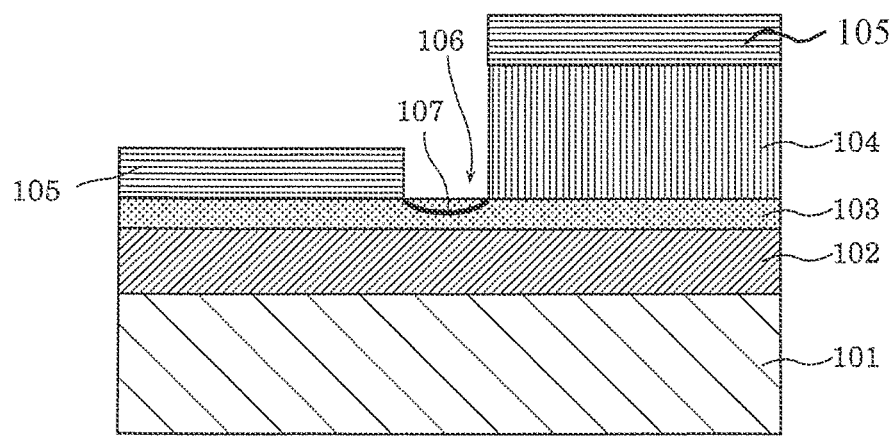
FIG. 2D is a cross-sectional view illustrating an example of the manufacturing method of the gas sensor according to Embodiment 1.

Lastly, as illustrated in FIG. 2D, local region 107 illustrated in FIG. 1 is formed in gas-sensitive insulating film 103 by applying the initial breakdown voltage across first electrode 104 and second electrode 105, thereby completing gas sensor 100.

An example of a range of the voltage for forming local region 107 is described below with reference to FIG. 3.

Figure 3:
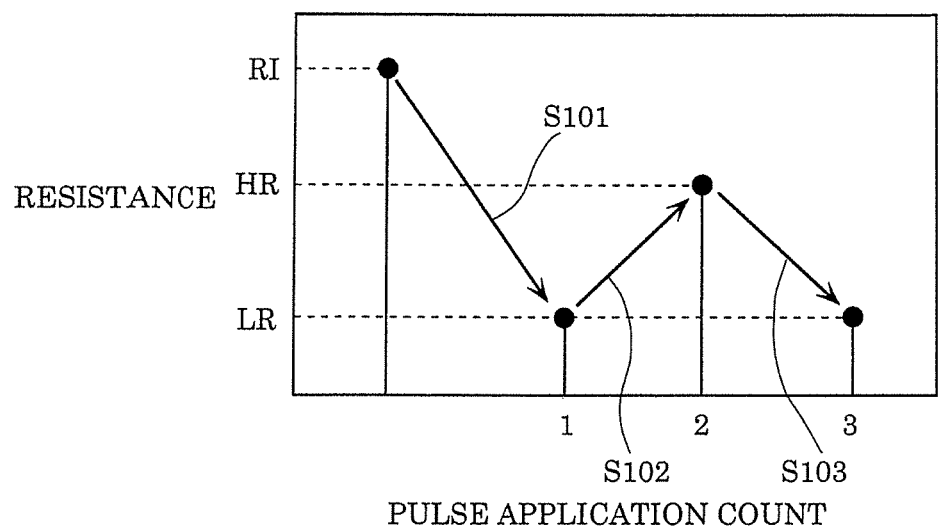
FIG. 3 is a graph showing the state of a gas sensing element according to Embodiment 1.

Gas sensor 100 that is a sample used in the measurement in FIG. 3 sets the film thickness of first electrode 104 to 25 nm and sets the film thickness of second electrode 105 to 13 nm. The pattern size of both electrodes is 1300 μm×550 μm.

The film thickness of gas-sensitive insulating film 103 is 5 nm, for example. As gas-sensitive insulating film 103, $TaO_y$ (y=2.47) that is oxide having a film thickness of 5 nm is used. In gas sensor 100 as above, when the voltage for reading (for example, 0.4 V) is applied across the electrodes, the initial resistance is from about $10^7 \Omega$ to about $10^8 \Omega$.

As shown in FIG. 3, when the resistance of gas sensor 100 is an initial resistance (A value, for example, from $10^7 \Omega$ to $10^8 \Omega$ that is higher than resistance (high resistance) HR in a high-resistance state. The value is an example, and the initial resistance is not limited to the value), the resistance state is changed to resistance (low resistance) LR in a low-resistance state by applying the initial breakdown voltage across the electrodes (S101). Then, when two types of voltage pulses of which pulse width is 100 ns and polarities are different from each other, that is, a positive voltage pulse and a negative voltage pulse, for example, are alternately applied between first electrode 104 and second electrode 105 of gas sensor 100 as the voltage for writing, the resistance of gas-sensitive insulating film 103 changes as shown in FIG. 3.

That is, when a positive voltage pulse (pulse width of 100 ns) is applied between first electrode 104 and second electrode 105 as the voltage for writing, the resistance of gas-sensitive insulating film 103 increases to high resistance HR from low resistance LR (S102). Meanwhile, when a negative voltage pulse (pulse width of 100 ns) is applied between first electrode 104 and second electrode 105 as the voltage for writing, the resistance of gas-sensitive insulating film 103 decreases to low resistance LR from high resistance HR (S103). In other words, the metal oxide layer forming gas-sensitive insulating film 103 reversibly transitions to a high-resistance state and a low-resistance state on the basis of the voltage applied across first electrode 104 and second electrode 105. Note that the polarity of the voltage pulse is "positive" when the potential of second electrode 105 is high with respect to the potential of first electrode 104, and is "negative" when the potential of second electrode 105 is low with respect to the potential of first electrode 104.

An evaluation example of a resistance change characteristic of the hydrogen-containing gas of gas sensor 100 formed as above is described.

Figure 4A:
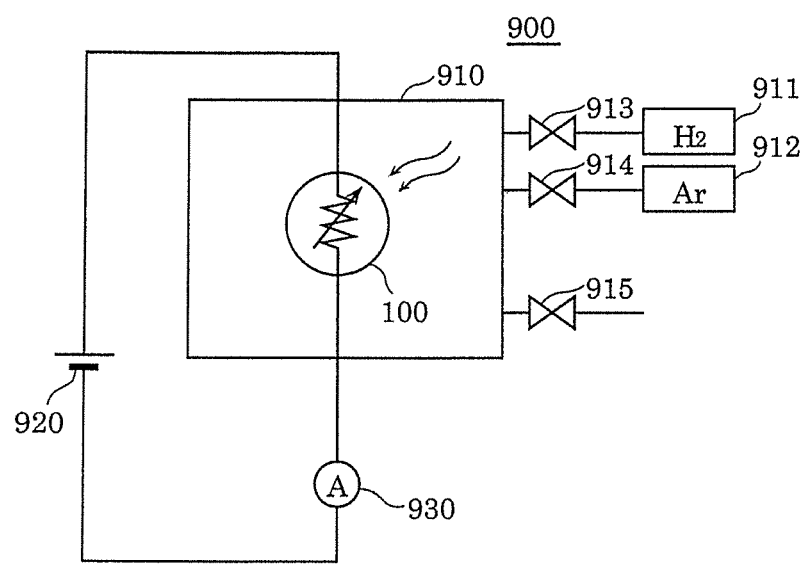
FIG. 4A is a diagram illustrating a gas evaluation system of the gas sensor according to Embodiment 1.

FIG. 4A is block diagram illustrating an example of gas evaluation system 900 used for the evaluation of gas sensor 100. Gas evaluation system 900 illustrated in FIG. 4A includes sealed container 910 that stores therein gas sensor 100, power supply 920, and current measuring instrument 930. Sealed container 910 is connected to hydrogen gas cylinder 911 and argon gas cylinder 912 via introduction valves 913 and 914, respectively, and is able to discharge the internal gas via exhaust valve 915. In gas sensor 100, power supply 920 is a power supply circuit that constantly applies a predetermined voltage across first electrode 104 and second electrode 105. Current measuring instrument 930 is a measurement circuit that measures the current flowing through gas-sensitive insulating film 103 when a predetermined voltage is applied across first electrode 104 and second electrode 105 in gas sensor 100.

Figure 4B:
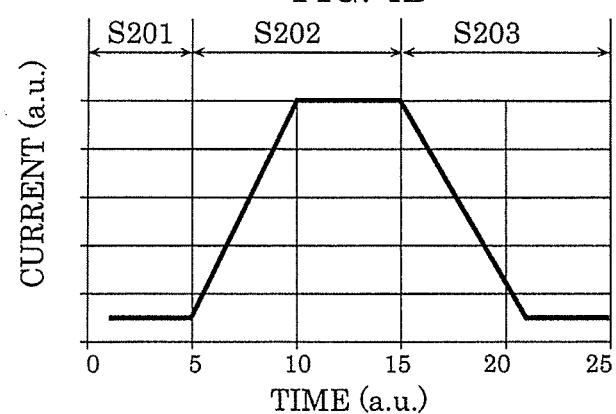
FIG. 4B is a graph showing an evaluation result of the gas sensor according to Embodiment 1.

FIG. 4B is a graph showing an evaluation example of gas sensor 100. The horizontal axis indicates the time (a.u.) and the vertical axis indicates the current (a.u.) flowing between first electrode 104 and second electrode 105. In the evaluation experiment, first, argon gas is introduced into sealed container 910 in which gas sensor 100 is placed. Then, argon gas is switched to hydrogen gas. Then, the hydrogen gas is further switched to argon gas.

FIG. 4B shows the result at this time, and the horizontal axis indicates three periods in which the former argon introduction (Step S201), the hydrogen introduction (Step S202), and the latter argon introduction (Step S203) are performed. It can be seen that the current starts to increase after the introduced gas is switched from argon gas to hydrogen gas. In addition, it can be seen that the current starts to decrease after the introduced gas is switched from hydrogen gas to argon gas.

In this evaluation example, gas sensor 100 in which local region 107 is set to a high-resistance state by applying a predetermined voltage (potential difference) across first electrode 104 and second electrode 105 in advance is used. In the monitoring operation of the hydrogen-containing gas, a gas sensing voltage of 0.6 V is applied across first electrode 104 and second electrode 105, and the current of from 10 μA to 20 μA flows between first electrode 104 and second electrode 105 in a state in which the hydrogen gas is detected. Therefore, according to gas sensor 100, it can be seen that the hydrogen-containing gas can be monitored with extremely small electricity consumption of from 0.006 mW to 0.012 mW.

From the result above, the detection mechanism of the hydrogen gas in gas sensor 100 is assumed to be as follows.

When the hydrogen-containing gas comes into contact with second electrode 105, the hydrogen atoms are dissociated from the hydrogen-containing gas by the catalysis caused by second electrode 105. In order to maintain an equilibrium state, the dissociated hydrogen atoms are diffused in second electrode 105 and reach local region 107 in the region of gap 106.

By the hydrogen atoms, a reduction reaction occurs in very small local region 107, and the degree of oxygen deficiency in local region 107 increases. As a result, the connection of the filaments in local region 107 becomes easier, and the resistance of local region 107 decreases. As a result, it is conceived that the current flowing between first electrode 104 and second electrode 105 increases.

Conversely, when there is no hydrogen-containing gas near second electrode 105, the dissociated hydrogen atoms become hydrogen molecules near the surface of second electrode 105 in order to maintain an equilibrium state, and leaves the surface of second electrode 105 to the outside.

Accordingly, the hydrogen atoms that have formed the water molecules in local region 107 returns to second electrode 105 by a reduction reaction. Meanwhile, the oxygen that has formed the water molecules becomes bound to the oxygen defect, thereby reducing the degree of oxygen deficiency.

As a result, it is conceived that it becomes difficult for the filaments in local region 107 to be connected, and the resistance increases. As a result, the current flowing between first electrode 104 and second electrode 105 decreases.

In addition, it is conceived that, in the abovementioned operation, the detectable gas is not limited to hydrogen gas, and the abovementioned operation occurs for various types of hydrogen-containing gas such as methane and alcohol, for example.

As described above, according to gas sensor 100 according to this embodiment, a detecting element with excellent power-saving properties capable of generating heat with only the current for sensing the resistance state and detecting the hydrogen-containing gas without heating with a separate heater can be obtained.

[Effect of Material of Second Electrode]

Figure 5A:
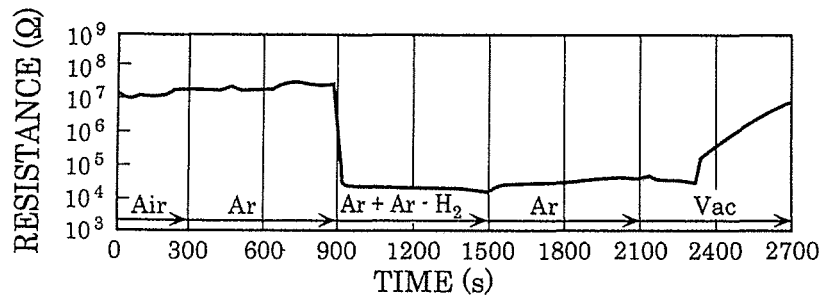
FIG. 5A is a graph showing the resistance measurement result after the gas is introduced when a second electrode of the gas sensor according to Embodiment 1 is Pt.
Figure 5B:
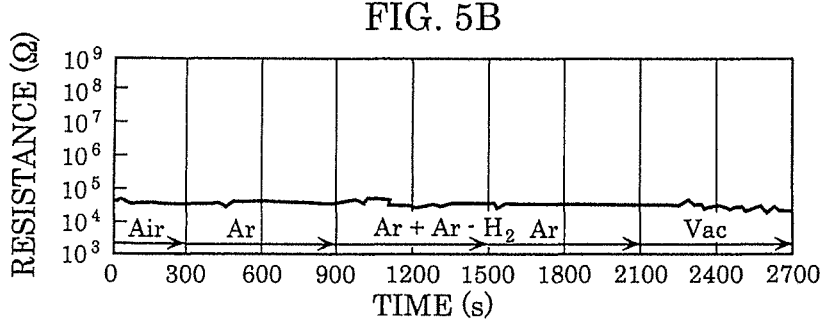
FIG. 5B is a graph showing the resistance measurement result after the gas is introduced when the second electrode of the gas sensor according to Embodiment 1 is TiN.

Now, the effect of the material of second electrode 105 is examined in order to check the mechanism of gas sensor 100. Specifically, gas sensor 100 in which the material of second electrode 105 is Pt that causes catalysis with respect to hydrogen and gas sensor 100 in which the material of second electrode 105 is TiN that does not cause catalysis with respect to hydrogen are generated. Then, the change in resistance is measured when hydrogen/argon gas of which hydrogen concentration is 4% is introduced for each of a case in which second electrode 105 is Pt and a case in which second electrode 105 is TiN. The measurement results at this time are shown in FIG. 5A and FIG. 5B. FIG. 5A is a graph showing the resistance measurement result after the gas is introduced when second electrode 105 of gas sensor 100 is Pt. FIG. 5B is a graph showing the resistance measurement result after the gas is introduced when second electrode 105 of gas sensor 100 is TiN.

In the resistance measurement, gas sensor 100 is arranged in a sealed container, and measurement is performed by introducing air atmosphere (Air) into the sealed container from time point 0 s to time point 300 s, introducing argon atmosphere (Ar) into the sealed container from time point 300 s to time point 900 s, introducing hydrogen/argon gas (Ar—$H_2$) in addition to argon atmosphere (Ar) into the sealed container from time point 900 s to time point 1500 s, introducing argon atmosphere (Ar) into the sealed container again from time point 1,500 s to time point 2,100 s, and performing vacuum drawing (Vac) of the sealed container from time point 2,100 s to time point 2,700 s.

As shown in FIG. 5A, when the material of second electrode 105 is Pt that causes catalysis, the resistance of gas sensor 100 decreases by about three digits when the hydrogen/argon gas is introduced to the argon atmosphere (the period of Ar+Ar—$H_2$ shown in FIG. 5A). Further, by completely removing hydrogen gas by performing vacuum drawing on sealed container 910 (the period of Vac shown in FIG. 5A), the resistance of gas sensor 100 recovers to the original value again. Meanwhile, as shown in FIG. 5B, when the material of second electrode 105 is TiN that does not cause catalysis, a change in the resistance of gas sensor 100 cannot be seen even when the hydrogen/argon gas is introduced into the sealed container of the argon atmosphere (the period of Ar+Ar—$H_2$ shown in FIG. 5B).

From those results, it is conceived that a material that causes catalysis is necessary for second electrode 105, and the hydrogen gas is dissociated into hydrogen atoms when the catalysis occurs on the electrode surface.

[Gas Introducing Speed]

Figure 6:
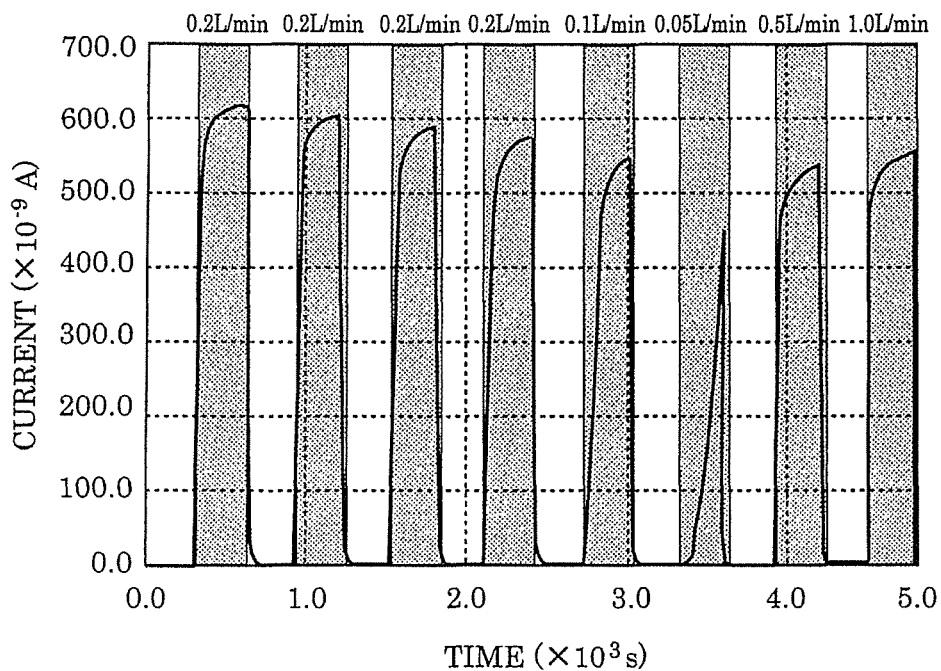
FIG. 6 is a graph showing the measurement result of the gas introduction flow rate and the output current of the gas sensor according to Embodiment 1.

In addition, the relationship between the reaction time of gas sensor 100 and the gas flow rate of the hydrogen/argon gas to be introduced is examined. FIG. 6 is a graph showing the measurement result of the gas introduction flow rate and the sensor output current of gas sensor 100. Note that the shaded parts in FIG. 6 indicate a time zone in which the hydrogen gas is introduced, and the introduced gas flow rate is the value described on the upper part of FIG. 6.

As illustrated in FIG. 6, the output current of gas sensor 100 greatly increases by introducing the hydrogen/argon gas into the sealed container, and the output current of gas sensor 100 decreases by stopping the hydrogen/argon gas introduction. Further, it can be understood from FIG. 6 that the rising of the current measurement value becomes faster in accordance with the increase in the gas flow rate of the hydrogen/argon gas to be introduced. With use of the relationship, the hydrogen gas concentration can be measured by measuring the time until the current reaches a predetermined current from the introduction of the hydrogen/argon gas.

[Effect of Forming]

Figure 7:
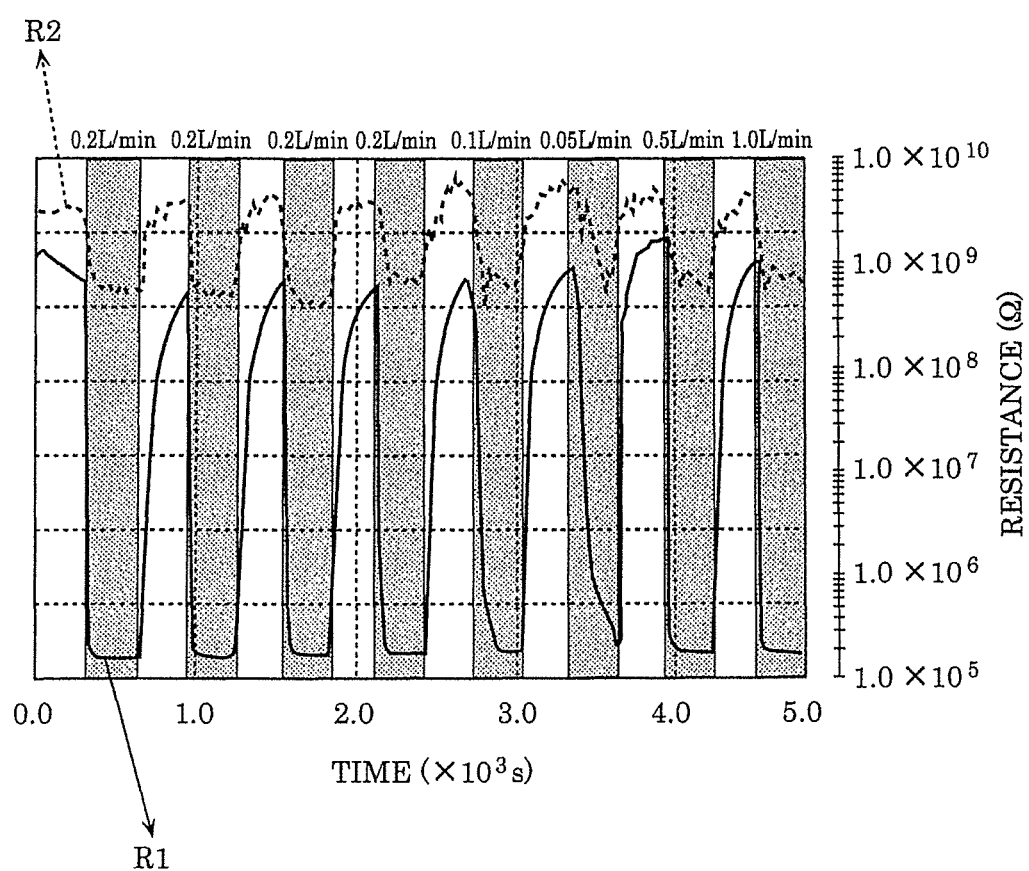
FIG. 7 is a graph showing the measurement result of the gas introduction flow rate and the resistance in accordance with whether there is forming of the gas sensor according to Embodiment 1.

Next, the effect of the resistance change of gas sensor 100 due to the forming state is examined. FIG. 7 is a graph showing the measurement result of the gas introduction flow rate and the resistance in accordance with whether there is forming of gas sensor 100. Note that the shaded parts in FIG. 7 indicate time zones in which the hydrogen gas is introduced, and the introduced gas flow rate in each time zone is the value described on the upper portion of FIG. 7.

As indicated by solid line R1 in FIG. 7, in gas sensor 100 with forming, the resistance decreases by three digits by the introduction of the hydrogen/argon gas. In addition, as with the result in FIG. 6, the time until the state reaches a low-resistance state becomes shorter as the gas flow rate of the hydrogen/argon gas increases. The resistance decreases by the introduction of the hydrogen/argon gas also in gas sensor 100 without the forming process indicated by dotted line R2 in FIG. 7, but the change does not go further than a change by about one digit. This is assumed to be caused by the state of the local region being different from the case with the forming process and the oxygen lacking density being low in the local region of the gas sensor without the forming.

From the results, the gas detection sensitivity of gas sensor 100 can be adjusted by controlling the state of the local region, that is, the oxygen lacking density in the local region by the forming process.

[Gas Sensing Voltage]

Figure 8A:
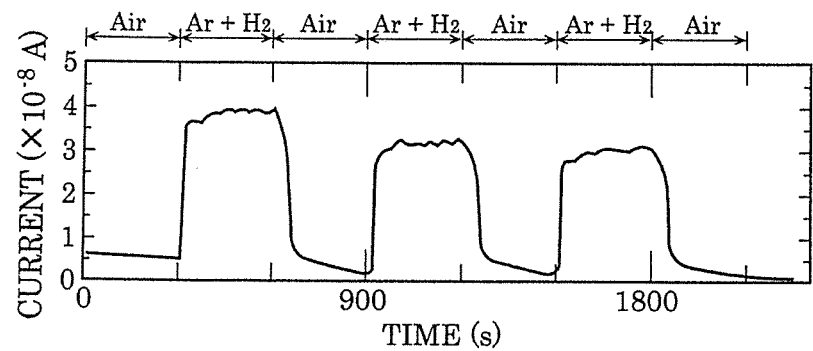
FIG. 8A is a graph showing the measurement result of the gas sensing voltage and the output current of the gas sensor according to Embodiment 1.
Figure 8B:
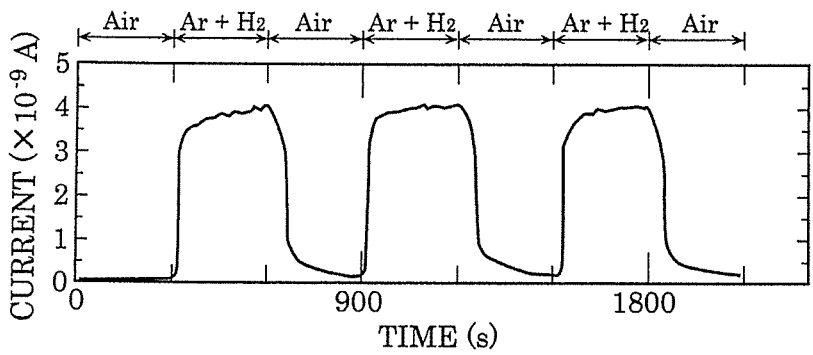
FIG. 8B is a graph showing the measurement result of the gas sensing voltage and the output current of the gas sensor according to Embodiment 1.
Figure 8C:
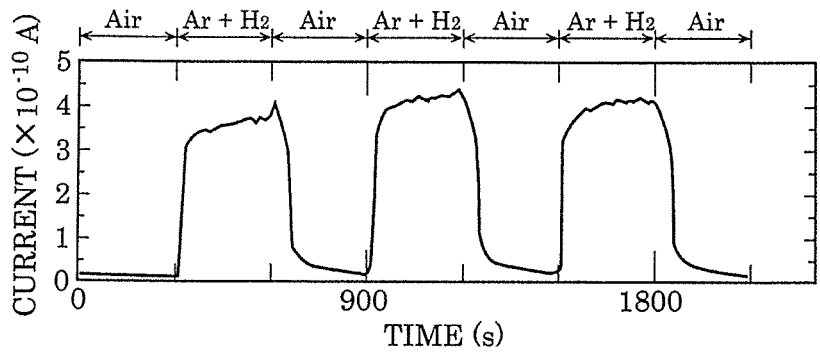
FIG. 8C is a graph showing the measurement result of the gas sensing voltage and the output current of the gas sensor according to Embodiment 1.

Further, the dependency of the gas sensing voltage is examined for gas sensor 100 in which second electrode 105 is formed by Pt. FIG. 8A to FIG. 8C are graphs showing the measurement result of the gas sensing voltage and the output current of gas sensor 100. FIG. 8A to FIG. 8C each show the output current when gas sensing voltage $V_{READ}$ is 100 mV, 10 mV, and 1 mV, respectively. Note that FIG. 8A to FIG. 8C alternately repeat the period in which the hydrogen/argon gas of 0.5 L/min is introduced (the period of Ar+$H_2$ shown in FIG. 8A to FIG. 8C) and the period in which air is introduced (the period of Air shown in FIG. 8A to FIG. 8C) every 30 s.

As illustrated in FIG. 8A, when gas sensing voltage $V_{READ}$ is 100 mV, the resistance decreases and a current of 35 nA is sensed when the hydrogen/argon gas is introduced to gas sensor 100. Further, when gas sensing voltage $V_{READ}$ is reduced to 10 mV and 1 mV, the detected current decreases to $\frac{1}{10}$ and $\frac{1}{100}$, respectively, in accordance with the decrease in voltage as shown in FIG. 8B and FIG. 8C. The gas sensing voltage has little effect on the rising situation of the current after the hydrogen/argon gas is introduced. Therefore, in gas sensor 100, gas sensing voltage $V_{READ}$ can be reduced to a voltage of at least about 1 mV. In other words, the electricity consumption does not necessarily need to be about 100 mW as in the gas sensing device of the related art when the gas detecting element is heated to 100° C. or more, and energy conservation and long life can be expected at the same time.

As described above, in gas sensor 100, the presence of gas can be sensed with a low gas sensing voltage and at high speed. Therefore, the gas containing hydrogen atoms can be sensed with low electricity consumption and at high speed.

Embodiment 2

Figure 9:
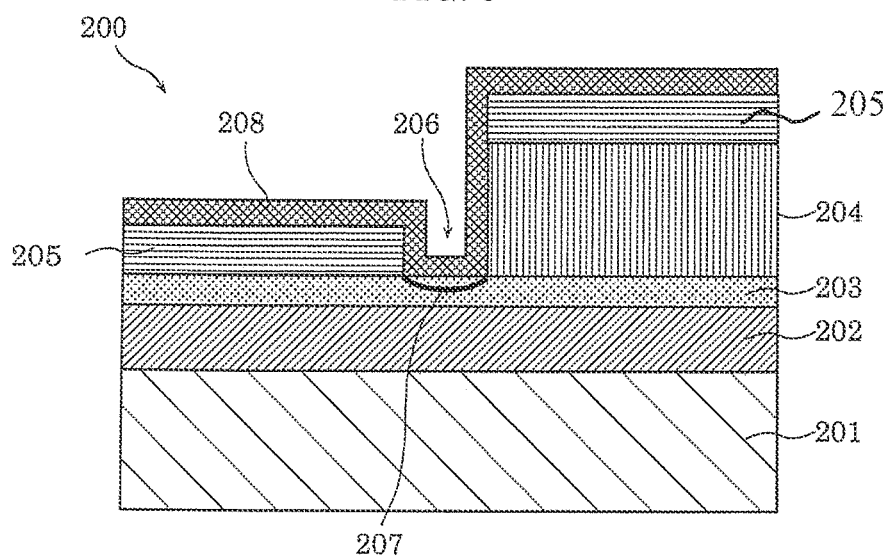
FIG. 9 is a cross-sectional view illustrating an example of the configuration of a gas sensor according to Embodiment 2.

FIG. 9 is a cross-sectional view illustrating a configuration example of gas sensor 200 according to Embodiment 2. Only the differences from gas sensor 100 according to Embodiment 1 are described below.

Gas sensor 200 illustrated in FIG. 9 includes substrate 201, interlayer insulating film 202, gas-sensitive insulating film 203, first electrode 204, second electrode 205, and gap 206. In addition, insulator layer 208 is formed so as to cover first electrode 204, second electrode 205, and gas-sensitive insulating film 203 in gap 206. Note that insulator layer 208 only needs to be formed so as to at least cover gas-sensitive insulating film 203 in gap 206.

Insulator layer 208 has a function of selectively causing hydrogen gas to pass therethrough (in other words, a function of causing the hydrogen gas to easily pass therethrough but not causing gas other than the hydrogen gas to easily pass therethrough). As a result, gas-sensitive insulating film 203 does not directly come into contact with gas, and hence it is effective in terms of improving the reliability of the sensor operation. Note that insulator layer 208 is formed by a silicon oxide film, for example.

The function of insulator layer 208 for selectively causing hydrogen gas to pass therethrough depends on the film thickness of insulator layer 208. For example, when insulator layer 208 is a silicon oxide film and the film thickness of insulator layer 208 is too thin, the electrons in second electrode 205 may be transmitted through insulator layer 208 to leak out, and then interact with molecules from the outside, which may cause the adsorption of the molecules, the dissociation of the hydrogen atoms from the molecules, or the like. Then, it is hard to say that the passing of gas other than the hydrogen gas is suppressed. Therefore, the film thickness of insulator layer 208 is preferred to be a film thickness by which the number of hydrogen molecules necessary for changing the resistance of the metal oxide layer are transmitted within a predetermined amount of time.

The thickness of insulator layer 208 for not causing gas other than the hydrogen gas to pass therethrough may be 8.5 nm, for example, as described below. The lower limit of the thickness of insulator layer 208 may be 0.5 nm, for example, on the basis of the disclosure of NPL 5.

Figure 10A:
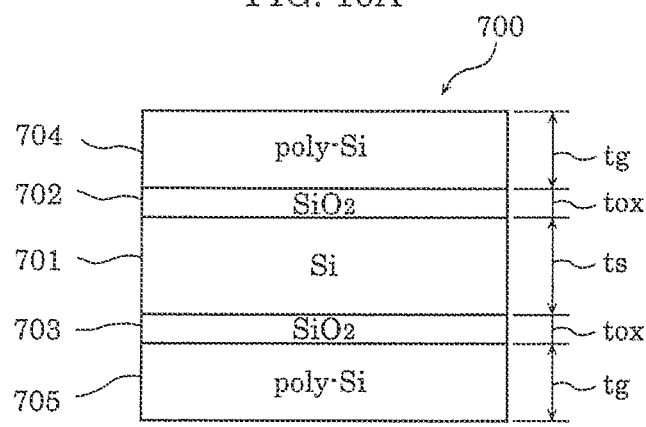
FIG. 10A is a cross-sectional view illustrating an example of the configuration of a double gate-silicon on insulator (DG-SOI) structure.

FIG. 10A is a cross-sectional view of structure body 700 having a double gate-silicon on insulator (DG-SOI) structure described in NPL 5. Structure body 700 is contemplated as a structure body obtained by forming silicon oxide films 702 and 703 on upper and lower main surfaces of silicon substrate 701, and further depositing polysilicon films 704 and 705 on exposed surfaces of silicon oxide films 702 and 703. For the purpose of calculation, a thickness ts of silicon substrate 701 and a thickness tg of each polysilicon film are 5 nm, and a thickness tox of each of silicon oxide films 702 and 703 is controlled.

Figure 10B:
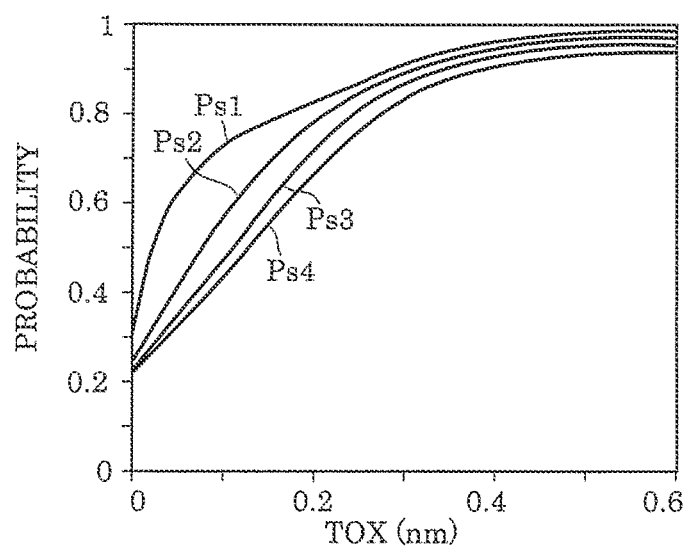
FIG. 10B is a graph showing the relationship between the existence probability of electrons and the thickness of a silicon oxide film.

FIG. 10B shows a result obtained by calculating the existence probability ($P_{s1}$ to $P_{s4}$) of the electrons in silicon substrate 701 by changing the thickness tox of each of silicon oxide films 702 and 703 in structure body 700. In FIG. 10B, $P_{s1}$ to $P_{s4}$ correspond to the energy levels of the electrons in silicon substrate 701 in the DG-SOI structure illustrated in FIG. 10A, and indicate the existence probability of the electrons on the orbits thereof. In any of $P_{s1}$ to $P_{s4}$, when tox becomes 0.5 nm or less, the existence probability of the electrons in silicon substrate 701 becomes significantly smaller than 1. This means that the electrons in silicon substrate 701 are passing through silicon oxide films 702 and 703 and are leaking out to polysilicon films 704 and 705. In any of $P_{s1}$ to $P_{s4}$, when tox is 0.5 nm or more, the existence probability of the electrons in silicon substrate 701 becomes about 1. This means that the electrons in silicon substrate 701 cannot pass through silicon oxide films 702 and 703 and do not leak out to polysilicon films 704 and 705.

From the calculation result, the electrons cannot substantially pass through a silicon oxide film of which film thickness tox is 0.5 nm or more. Therefore, by depositing a silicon oxide film having a thickness of 0.5 nm or more on second electrode 205, the electrons in second electrode 205 can be prevented from interacting with the molecules existing on the outside. As a result, external gas is not adsorbed by the surface of second electrode 205, and the hydrogen atoms are not dissociated from the molecules containing the hydrogen atoms at second electrode 205 that causes catalysis.

Note that it is not always true that it is better when the thickness of the silicon oxide film is thicker. When silicon oxide film is too thick, it requires time for gas-sensitive insulating film 203 to cause resistance change by the hydrogen molecules that have passed through the silicon oxide film and reached second electrode 205. Therefore, there is an upper limit to the thickness of the silicon oxide film in order to realize a desired response time (for example, within one second as a standard desired for the gas sensor used for a fuel cell vehicle).

In gas sensor 200, the number of hydrogen molecules that need to reach second electrode 205 in order to cause gas-sensitive insulating film 203 set to be in a high-resistance state to transition to a low-resistance state depends on the material and the size of gas sensor 200. In a specific example of the gas sensor examined by the inventors of the present disclosure, the number is 2,200. In other words, in the gas sensor, at least 2,200 hydrogen molecules are required to pass through the silicon oxide film and reach second electrode 205 within one second.

Figure 10C:
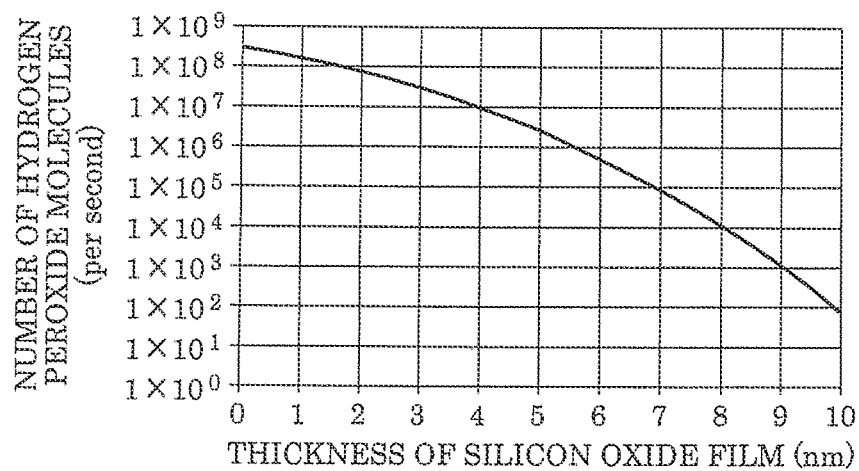
FIG. 10C is a graph showing the relationship between the number of hydrogen molecules transmitted through the silicon oxide film in one second and the film thickness of the silicon oxide film.

When hydrogen gas having a hydrogen molecule density of $N_0$ exists on the silicon oxide film surface, and the number of the hydrogen molecules transmitted through the silicon oxide film in t second is expressed by n, n is obtained by the following expression.

$$n = N_0 A \sqrt{\frac{K_B T}{2\pi M}} \, \text{erfc}\left(\frac{x_1}{2\sqrt{D_{SiO2} L}}\right) \quad \text{(Expression 1)}$$

n: number of transmitted hydrogen molecules after t second
$x_1$: thickness of the silicon oxide film
$N_0$: hydrogen molecule density
A: filament area
$K_B$: Boltzmann constant
T: Kelvin temperature
M: hydrogen molecule mass
$D_{SiO2}$: diffusion coefficient (in $SiO_2$) of the hydrogen molecules
t: time FIG. 10C is a graph showing the result obtained by calculating the relationship between the number of hydrogen molecules transmitted through the silicon oxide film in one second and the film thickness of the silicon oxide film when hydrogen molecule density $N_0$ is 0.1% on the basis of Expression 1. The dotted line indicates 2,200 that is an example of the number of hydrogen molecules necessary for the resistance change of gas-sensitive insulating film 203. It can be seen from FIG. 10C that 2,200 hydrogen molecules necessary for the resistance change reach the surface of second electrode 205 within one second when the thickness of silicon oxide film is 8.5 nm or less.

As described above, by causing the thickness tox of the silicon oxide film to be within a desired range, the leaking of the hydrogen molecules to polysilicon films 704 and 705 can be suppressed. In addition, 2,200 hydrogen molecules necessary for the resistance change can be caused to reach the surface of second electrode 205 within a desired response time. As an example, the thickness tox of the silicon oxide film may be 0.5 nm or more and 8.5 nm or less for the gas sensor used for the fuel cell vehicle. As a result, the leaking of the hydrogen molecules to polysilicon films 704 and 705 can be suppressed. In addition, 2,200 hydrogen molecules necessary for the resistance change can be caused to reach the surface of second electrode 205 within a desired response time (within one second for the gas sensor used for the fuel cell vehicle).

Embodiment 3

FIG. 11A, FIG. 11B, FIG. 11C, and FIG. 11D are cross-sectional views illustrating configuration examples of gas sensors according to Embodiment 3. Only parts of gas sensors 300, 400, 500, and 600 according to this embodiment that are different from gas sensor 100 according to Embodiment 1 are described below.

[Configuration 1]

Figure 11A:
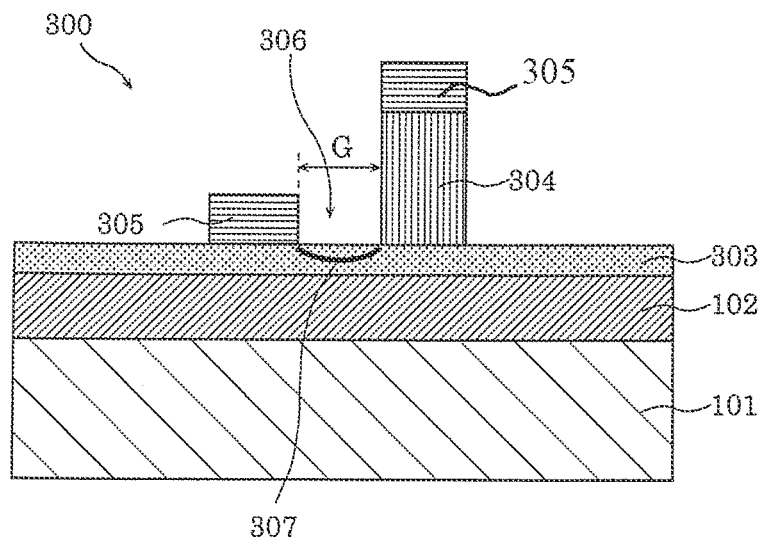
FIG. 11A is a cross-sectional view illustrating an example of the configuration of a gas sensor according to Embodiment 3.

In gas sensor 300 illustrated in FIG. 11A, on interlayer insulating film 102 formed on substrate 101, gas-sensitive insulating film 303 is formed in a region that is larger than first electrode 304 and second electrode 305. Note that substrate 101 and interlayer insulating film 102 are similar to substrate 101 and interlayer insulating film 102 of gas sensor 100 illustrated in Embodiment 1, and hence the description thereof is omitted.

As a result, only first electrode 304 and second electrode 305 of the minimum width need to be arranged on gas-sensitive insulating film 303. Therefore, local region 307 can be efficiently formed on gas-sensitive insulating film 303. Therefore, gas sensor 300 can be formed by efficiently arranging first electrode 304 and second electrode 305.

[Configuration 2]

Figure 11B:
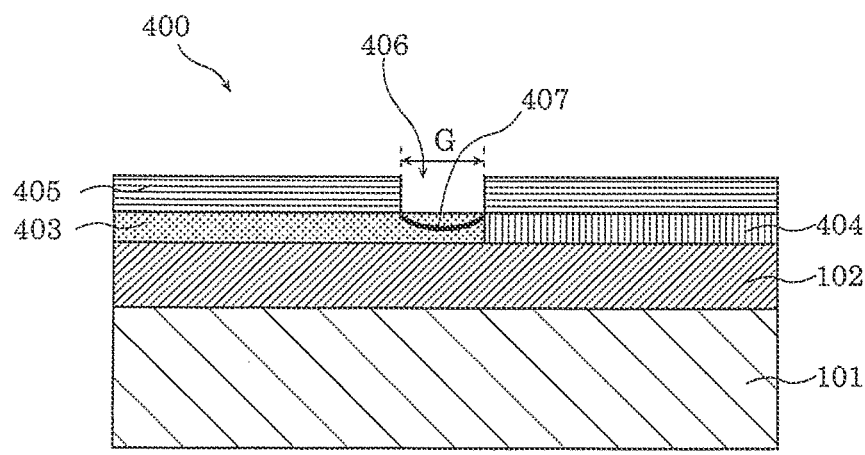
FIG. 11B is a cross-sectional view illustrating an example of the configuration of the gas sensor according to Embodiment 3.

Gas sensor 400 illustrated in FIG. 11B has a structure in which, on interlayer insulating film 102 formed on substrate 101, gas-sensitive insulating film 403 is in contact with an end surface of at least one of first electrode 404 and second electrode 405. In other words, one of first electrode 404 and second electrode 405 is arranged at the same layer level as gas-sensitive insulating film 403, and the other is arranged on gas-sensitive insulating film 403. Further, in planar view, a region in which gas-sensitive insulating film 403 is exposed is provided between a region in which first electrode 404 is arranged and a region in which second electrode 405 is arranged. Note that substrate 101 and interlayer insulating film 102 are similar to substrate 101 and interlayer insulating film 102 of gas sensor 100 described in Embodiment 1, and hence the description thereof is omitted.

As a result, local region 407 is formed between an end surface of first electrode 404 or second electrode 405 arranged at the same layer level as gas-sensitive insulating film 403 and second electrode 405 or first electrode 404 arranged on gas-sensitive insulating film 403. In addition, the surface of gas-sensitive insulating film 403 other than the part in which local region 407 is desired to be formed is covered with first electrode 404 or second electrode 405. Therefore, the reaction of gas-sensitive insulating film 403 with other gas in parts other than the part in which local region 407 is formed can be suppressed.

[Configuration 3]

Figure 11C:
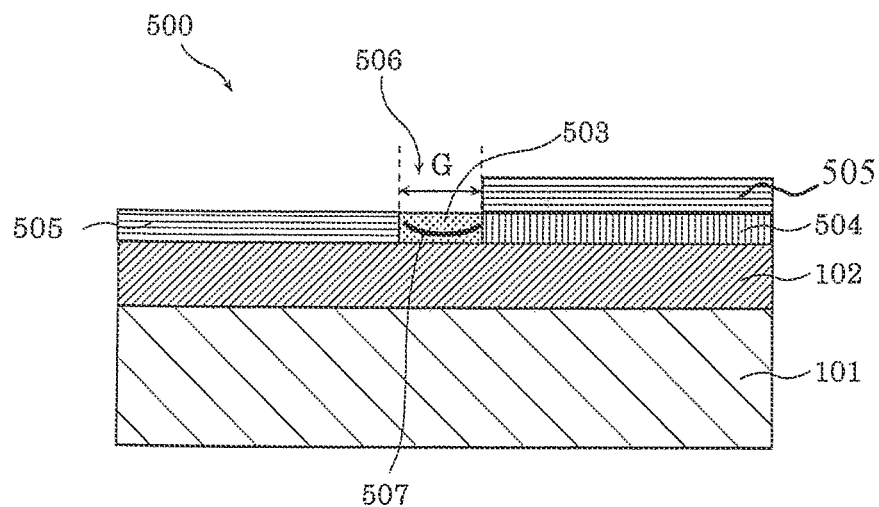
FIG. 11C is a cross-sectional view illustrating an example of the configuration of the gas sensor according to Embodiment 3.

Gas sensor 500 illustrated in FIG. 11C has a structure in which, on interlayer insulating film 102 formed on substrate 101, gas-sensitive insulating film 503 in contact with end surfaces of both of first electrode 504 and second electrode 505. In other words, first electrode 504 and second electrode 505 are arranged at the same layer level as gas-sensitive insulating film 503. Further, a region in which gas-sensitive insulating film 503 is exposed is provided between a region in which first electrode 504 is arranged and a region in which second electrode 505 is arranged in planar view. Note that substrate 101 and interlayer insulating film 102 are similar to substrate 101 and interlayer insulating film 102 of gas sensor 100 described in Embodiment 1, and hence the description thereof is omitted.

As a result, by applying voltage between the end surface of first electrode 504 and the end surface of second electrode 505 in gas-sensitive insulating film 503 exposed between the region in which first electrode 504 is arranged and the region in which second electrode 505 is arranged, local region 507 can be easily formed in gas-sensitive insulating film 503. In addition, the surface of gas-sensitive insulating film 503 other than the part in which local region 507 is desired to be formed is covered with first electrode 504 or second electrode 505. Therefore, the reaction of gas-sensitive insulating film 503 with other gas in parts other than the part in which local region 507 is formed can be suppressed.

[Configuration 4]

Figure 11D:
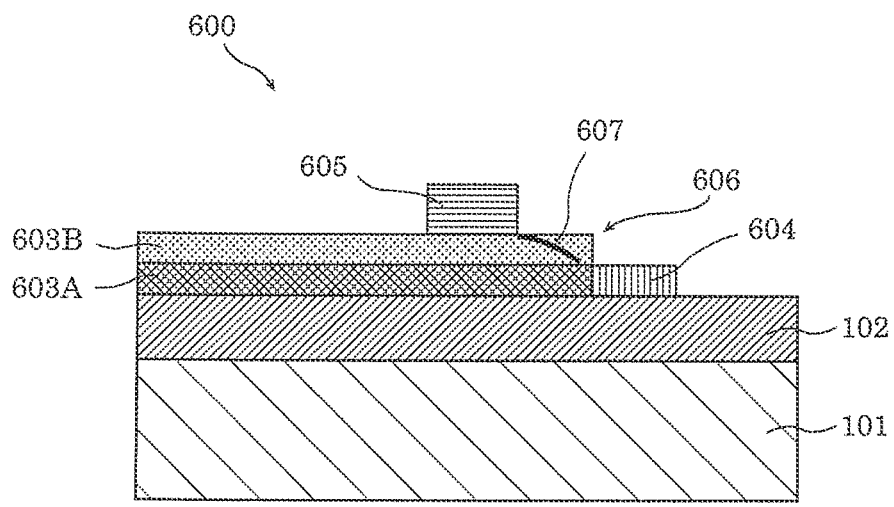
FIG. 11D is a cross-sectional view illustrating an example of the configuration of the gas sensor according to Embodiment 3.

Gas sensor 600 illustrated in FIG. 11D includes two layers, that is, first oxide layer 603A and second oxide layer 603B as the gas-sensitive insulating film on interlayer insulating film 102 formed on substrate 101. Note that the gas-sensitive insulating film may be formed by two or more layers. Substrate 101 and interlayer insulating film 102 are similar to substrate 101 and interlayer insulating film 102 of gas sensor 100 described in Embodiment 1, and hence the description thereof is omitted.

First oxide layer 603A and second oxide layer 603B are laminated on a part of interlayer insulating film 102 in the stated order. In addition, first electrode 604 is formed on interlayer insulating film 102 so as to be continuous to first oxide layer 603A. In other words, an end portion of first oxide layer 603A is connected with an end portion of first electrode 604. In addition, second electrode 605 is formed on at least a part of second oxide layer 603B.

Further, local region 607 arranged in contact with second electrode 605 and not in contact with first electrode 604 is included in first oxide layer 603A and second oxide layer 603B.

At least a part of local region 607 is formed in second oxide layer 603B, and the degree of oxygen deficiency of local region 607 reversibly changes in accordance with the application of an electrical pulse. It is conceived that local region 607 includes a filament formed by oxygen defection sites.

In other words, gas-sensitive insulating film 603 has a laminated structure at least including first oxide layer 603A including first metal oxide and second oxide layer 603B including second metal oxide. Further, first oxide layer 603A is arranged between first electrode 604 and second oxide layer 603B, and second oxide layer 603B is arranged between first oxide layer 603A and second electrode 605. The thickness of second oxide layer 603B may be thinner than the thickness of first oxide layer 603A. In this case, a structure in which local region 607 is not in contact with first electrode 604 described below can be easily formed. The resistance of second oxide layer 603B is higher than the resistance of first oxide layer 603A, and hence most voltage applied to gas-sensitive insulating film 603 is applied to second oxide layer 603B.

In addition, in this disclosure, when the metal forming first oxide layer 603A and second oxide layer 603B is the same, a term "oxygen content" may be used in place of the "degree of oxygen deficiency". The expression "the oxygen content is high" corresponds to the expression "the degree of oxygen deficiency is small", and the expression "the oxygen content is low" corresponds to the expression "the degree of oxygen deficiency is large". However, gas-sensitive insulating film 603 according to this embodiment is not limited to the case where the metal forming first oxide layer 603A and second oxide layer 603B is the same, and the metal may be different. That is, first oxide layer 603A and second oxide layer 603B may be different metal oxides.

When a first metal forming first oxide layer 603A and a second metal forming second oxide layer 603B are the same, the oxygen content is in a corresponding relationship with the degree of oxygen deficiency. That is, when the oxygen content of the second metal oxide is larger than the oxygen content of the first metal oxide, the degree of oxygen deficiency of the first metal oxide is smaller than the degree of oxygen deficiency of the second metal oxide. The degree of oxygen deficiency of local region 607 is larger than the degree of oxygen deficiency of second oxide layer 603B, and is different from the degree of oxygen deficiency of first oxide layer 603A.

As described above, local region 607 is formed in at least one of first oxide layer 603A and second oxide layer 603B by applying an initial breakdown voltage across first electrode 604 and second electrode 605. For example, in gas sensor 600, it is conceived that the current easily flows through a region in which the distance between first electrode 604 and second electrode 605 is short. Therefore, by the initial breakdown, local region 607 is formed in a region that is in contact with second electrode 605, passes through second oxide layer 603B, partially enters first oxide layer 603A, and is not in contact with first electrode 604.

Embodiment 4

Fuel cell vehicle 800 according to Embodiment 4 includes any of the gas sensors described in Embodiment 1 to Embodiment 3 described above. Fuel cell vehicle 800 detects the hydrogen gas in the vehicle with the gas sensor.

Figure 12:
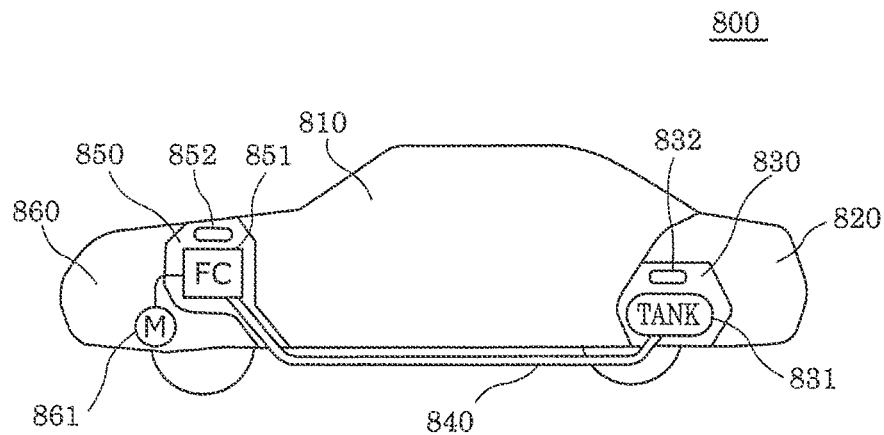
FIG. 12 is a side view illustrating an example of the configuration of a fuel cell vehicle according to Embodiment 4.

FIG. 12 is a side view illustrating a configuration example of fuel cell vehicle 800 according to this embodiment.

Fuel cell vehicle 800 includes passenger compartment 810, luggage compartment 820, gas tank compartment 830, fuel tank 831, gas sensor 832, piping 840, fuel cell compartment 850, fuel cell 851, gas sensor 852, motor compartment 860, and motor 861.

Fuel tank 831 is provided in gas tank compartment 830, and retains hydrogen gas as the fuel gas. Gas sensor 832 detects fuel gas leakage in gas tank compartment 830.

Fuel cell 851 is formed as a fuel cell stack by stacking cells each including a fuel electrode, an air electrode, and an electrolyte as a base unit. Fuel cell 851 is provided in fuel cell compartment 850. The hydrogen gas in fuel tank 831 is transmitted into fuel cell 851 in fuel cell compartment 850 through piping 840, and electricity is generated by causing the hydrogen gas and oxygen gas in the atmosphere to react with each other in fuel cell 851. Gas sensor 852 detects the leakage of hydrogen gas in fuel cell compartment 850.

Motor 861 is provided in motor compartment 860, rotates with the electricity generated by fuel cell 851, and causes fuel cell vehicle 800 to travel.

As described above, in the gas sensor according to this disclosure, hydrogen gas can be detected with extremely small electricity consumption of about 0.01 mW, for example. Therefore, the leakage of hydrogen gas can be constantly monitored without greatly increasing the standby power of the fuel cell vehicle by utilizing the excellent power-saving properties of the gas sensor.

For example, a predetermined voltage may be constantly applied to gas sensors 832 and 852 regardless of the operation state of an ignition key in fuel cell vehicle 800, and it may be determined whether there is hydrogen gas on the outside of fuel tank 831 in gas tank compartment 830 and the outside of fuel cell 851 in fuel cell compartment 850 on the basis of the current amount flowing through gas sensors 832 and 852.

As a result, for example, it is already determined whether there is leakage of hydrogen gas at the time point at which the operation of the ignition key is received, and hence the starting time of the fuel cell vehicle can be shortened as compared to when the gas sensor is driven in order to determine whether there is leakage of hydrogen gas after the operation of the ignition key is received. In addition, safety can be improved by continuing the monitoring of the leakage of hydrogen gas after the travel of the fuel cell vehicle, for example, after storing the fuel cell vehicle in a garage.

Other Embodiments

Although the gas sensor, the method of detecting hydrogen gas, and the fuel cell vehicle according to the aspects of the present disclosure have been described based on the above embodiments, the present discloser is not limited to the embodiments. Those skilled in the art will be readily appreciated that various modifications and combinations of the constituent elements and functions in the embodiments are possible without materially departing from the novel teachings and advantages of the present disclosure.

For example, the abovementioned gas sensor may further include a measurement circuit that measures the current flowing through the sensitive insulating film when a predetermined voltage is applied across the first electrode and the second electrode. In addition, a power supply circuit that constantly applies a predetermined voltage across the first electrode and the second electrode may be further included.

According to the configuration as above, a highly-convenient gas sensor can be obtained as a module part including a measurement circuit and a power supply circuit.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The gas sensor according to this disclosure is useful in a fuel cell vehicle, a hydrogen station, a hydrogen plant, and the like, for example.

What is claimed is:
1. A gas sensor, comprising:
a gas-sensitive body layer disposed above a substrate and including a metal oxide layer;
a first electrode, of which bottom surface is disposed at a same level as a bottom surface of the gas-sensitive body layer, and is disposed above the substrate, and not disposed on an upper surface of the gas-sensitive body layer; and
a second electrode disposed at the same layer level as a layer level of the gas-sensitive body layer above the substrate or disposed on the gas-sensitive body layer, the second electrode being apart from the first electrode by a gap, wherein:

the gas-sensitive body layer has a resistance change characteristic that reversibly transitions to a high-resistance state and a low-resistance state on basis of a voltage applied across the first electrode and the second electrode, at least a part of the gas-sensitive body layer is exposed to an area corresponding to the gap, and the gas-sensitive body layer has a resistance that decreases when gas containing a hydrogen atom is in contact with the second electrode.

2. The gas sensor according to claim 1, wherein the gas-sensitive body layer includes a local region corresponding to the gap, the local region has a degree of oxygen deficiency larger than a degree of oxygen deficiency of the metal oxide layer.

3. The gas sensor according to claim 2, wherein the gas-sensitive body layer is a laminated structure including (i) a first metal oxide layer comprising a first metal oxide and (ii) a second metal oxide layer comprising a second metal oxide, the second metal oxide having a degree of oxygen deficiency smaller than a degree of oxygen deficiency of the first metal oxide; and the local region passes through at least the second metal oxide layer, the local region being in contact with at least one of the first electrode and the second electrode, the local region having a degree of oxygen deficiency larger than a degree of oxygen deficiency of the second metal oxide layer.

4. The gas sensor according to claim 3, wherein at least one of the first metal oxide and the second metal oxide is a transition metal oxide.

5. The gas sensor according to claim 4, wherein the transition metal oxide is one of tantalum oxide, hafnium oxide, and zirconium oxide.

6. The gas sensor according to claim 2, wherein:

the second electrode comprises a material that causes catalysis that dissociates a hydrogen atom from a gas molecule containing the hydrogen atom; and a resistance of the metal oxide layer decreases as the hydrogen atom is dissociated from the gas molecule in a part of the second electrode in contact with the local region, and the dissociated hydrogen atom is bound to an oxygen atom in the local region of the metal oxide layer.

7. The gas sensor according to claim 1, wherein the second electrode comprises at least one of platinum, iridium, and palladium.

8. The gas sensor according to claim 1, further comprising:

a measurement circuit that measures a current flowing through the gas-sensitive body layer when a predetermined voltage is applied across the first electrode and the second electrode.

9. The gas sensor according to claim 8, wherein a concentration of the gas containing a hydrogen atom is determined by measuring time until the current flowing through the gas-sensitive body layer in the gas sensor reaches a predetermined current from start of introduction of the gas containing a hydrogen atom.

10. The gas sensor according to claim 1, comprising:

a power supply circuit that constantly applies a predetermined voltage across the first electrode and the second electrode.

11. The gas sensor according to claim 2, wherein an output value of a current flowing through the gas-sensitive body layer differs depending on a size and a resistance state of the local region.

12. A fuel cell vehicle, comprising:

a passenger compartment;

a gas tank compartment in which a tank of hydrogen gas is arranged;

a fuel cell compartment in which a fuel cell is arranged; and the gas sensor according to claim 1, wherein the gas sensor is arranged in at least one of the gas tank compartment and the fuel cell compartment.

13. The gas sensor according to claim 1, wherein the second electrode is disposed on the gas-sensitive body layer.

14. The gas sensor according to claim 1, wherein one side surface of the first electrode contacts a side surface of the gas-sensitive body layer and another side surface of the first electrode contacts no side surface of the gas-sensitive body layer.

* * * * *